United States Patent [19]
Powers

[11] Patent Number: 6,060,593
[45] Date of Patent: May 9, 2000

[54] INSULIN-DEPENDENT DIABETES MELLITUS-SPECIFIC CHIMERIC POLYPEPTIDES

[75] Inventor: Alvin C. Powers, Brentwood, Tenn.

[73] Assignee: Vanderbilt University, Nashville, Tenn.

[21] Appl. No.: 09/028,148

[22] Filed: Feb. 23, 1998

Related U.S. Application Data

[62] Division of application No. 08/592,696, Jan. 26, 1996, Pat. No. 5,821,334.

[51] Int. Cl.⁷ .................................................. C07H 21/04
[52] U.S. Cl. .......................................... 536/23.4; 536/23.2
[58] Field of Search .................................. 536/23.4, 23.2

[56] References Cited

U.S. PATENT DOCUMENTS 5,200,318   4/1993   Rabin et al. .

FOREIGN PATENT DOCUMENTS

WO 92/20811   11/1992   WIPO .
WO 94/12529   6/1994    WIPO .
WO94/18568    8/1994    WIPO ............................ G01N 33/53

OTHER PUBLICATIONS

Daw et al. Diabetes. vol. 44:216–220, Feb. 1995.

Noriko Ujihara, Kendra Daw, Roberto Gianani, Esper Boel, Liping Yu, and Alvin C. Powers: Identification of Glutamic Acid Decarboxylase Autoantibody Heterogeneity and Epitope Regions in Type I Diabetes, Diabetes, 43:968–975 (Aug. 1994).

Wiltrud Richter, Yuguang Shi and Steinunn Baekkeskov: Autoreactive Epitopes Defined by Diabetes–Associated Human Monoclonal Antibodies . . . , Proc. Natl. Acad. Sci. USA 90:2832–2836 (Apr. 1993).

Wiltrud Richter, Josef Endl, Thomas H. Eiermann, Michael Brandt, Rosemarie Kientsch–Engel, Charles Thivolet, Herbert Jungfer and Werner A. Scherbaum: Human Monoclonal Islet Cell Antibodies From a Patient With Insulin–Dependent Diabetes Mellitus Reveal Glutamate Decarboxylase as the Target Antigen, Proc. Natl. Acad. Sci. USA 89:8467–8471 (Sep. 1992).

Kendra Daw, Noriko Ujihara, Mark Atkinson, and Alvin C. Powers: Glutamic Acid Decarboxylase Autoantibodies in Stiff–Man Syndrome and Insulin=Dependent Diabetes Mellitus Exhibit Similarities and Differences in Epitope Recognition, The Journal of Immunology 156(2):818–25 (1996).

Kendra Daw and Alvin C. Powers: Two Distinct Glutamic Acid Decarboxylase Auto–Antibody Specificities in IDDM Target Different Epitopes, Diabetes 44(2):216–20 (Feb. 1995).

Michele Solimena, Ronald Dirkx, Jr., Michal Radzynski, Olaf Mundigi, and Pietro De Camilli: A Signal Located Within Amino Acids 1–27 of GAD65 is Required for Its Targeting to the Golgi Complex Region, The Journal of Cell Biology 126(2):331–341 (Jul. 1994).

*Primary Examiner*—Christina Y. Chan
*Assistant Examiner*—Patrick J. Nolan
*Attorney, Agent, or Firm*—Needle & Rosenberg, P.C.

[57] ABSTRACT

The present invention provides a chimeric polypeptide comprising an epitope of GAD65 protein and a structural region comprising a polypeptide of the GAD family, wherein the chimeric polypeptide is a more specific diagnostic for insulin dependent diabetes mellitus than intact GAD65 and produces fewer false positives than intact GAD65. The invention further provides a method of screening a subject for risk of developing IDDM, comprising contacting the chimeric polypeptide of claim 1 with a biological sample containing antibodies from the subject and detecting binding between an antibody in the biological sample and the chimeric polypeptide, the detection of binding indicating the subject is at risk of developing IDDM.

11 Claims, 1 Drawing Sheet

CHIMERIC GAD 65 and GAD 67 PROTEINS

A

GAD 65 (1-585)
GAD 67 (1-594)

B

GAD 67 (1-230)/GAD 65 (221-442)/GAD 67 (452-594)
(IDDM-E1)

GAD 67 (1-451)/GAD 65 (443-585)
(IDDM-E2)

C

Protein X/GAD 65 (221-585)

Protein X/GAD 65 (270-442)/Protein X

Protein X/GAD 65 (443-513)/Protein X/GAD 65 (528-585)

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:1:

```
ATGGCGTCTT CGACCCCATC TTCGTCCGCA ACCTCCTCGA ACGCGGGAGC GGACCCCAAT      60

ACCACTAACC TGCGCCCCAC AACGTACGAT ACCTGGTGCG GCGTGGCCCA TGGATGCACC     120

AGAAAACTGG GGCTCAAGAT CTGCGGCTTC TTGCAAAGGA CCAACAGCCT GGAAGAGAAG     180
```

-continued

```
AGTCGCCTTG TGAGTGCCTT CAAGGAGAGG CAATCCTCCA AGAACCTGCT TTCCTGTGAA      240

AACAGCGACC GGGATGCCCG CTTCCGGCGC ACAGAGACTG ACTTCTCTAA TCTGTTTGCT      300

AGAGATCTGC TTCCGGCTAA GAACGGTGAG GAGCAAACCG TGCAATTCCT CCTGGAAGTG      360

GTGGACATAC TCCTCAACTA TGTCCGCAAG ACATTTGATC GCTCCACCAA GGTGCTGGAC      420

TTTCATCACC ACACCAGTT GCTGGAAGGC ATGGAGGGCT TCAACTTGGA GCTCTCTGAC       480

CACCCCGAGT CCCTGGAGCA GATCCTGGTT GACTGCAGAG ACACCTTGAA GTATGGGGTT     540

CGCACAGGTC ATCCTCGATT TTTCAACCAG CTCTCCACTG GATTGGATAT TATTGGCCTA     600

GCTGGAGAAT GGCTGACATC AACGGCCAAT ACCAACATGT TTACATATGA AATTGCACCA     660

GTGTTTGTAC TACTGGAATA TGTGACACTA AAGAAAATGA GGGAAATCAT TGGCTGGCCA     720

GGAGGCTCTG GCGATGGAAT CTTTTCTCCT GGTGGTGCCA TCTCCAACAT GTACGCCATG     780

CTCATTGCCC GCTATAAGAT GTTTCCAGAA GTCAAGGAAA AGGGGATGGC GGCGGTGCCC     840

AGGCTCATCG CATTCACGTC AGAGCATAGT CACTTTTCTC TCAAGAAGGG AGCTGCAGCC     900

TTGGGGATCG GAACAGACAG CGTGATTCTG ATTAAATGTG ATGAGAGAGG GAAAATGATC     960

CCATCTGACC TTGAAAGAAG AATCCTTGAA GTCAAACAGA AAGGATTTGT TCCTTTCCTG    1020

GTGAGTGCCA CAGCTGGAAC CACTGTGTAC GGGGCTTTTG ATCCTCTCTT GGCTGTAGCT    1080

GACATCTGCA AAAAATATAA GATCTGGATG CATGTGGATG CTGCTTGGGG TGGAGGGTTA    1140

CTGATGTCTC GGAAACACAA GTGGAAGCTG AACGGTGTGG AGAGGGCCAA CTCTGTGACA    1200

TGGAATCCCC ACAAGATGAT GGGTGTCCCC TTGCAATGTT CGGCTCTCCT GGTCAGAGAG    1260

GAGGGACTGA TGCAGAGCTG CAACCAGATG CATGCTTCCT ACCTCTTTCA GCAAGATAAG    1320

CACTATGACC TGTCCTACGA CACCGGGGAC AAGGCAATTC AGTGTGGCCG CCACGTGGAT    1380

ATCTTCAAGT TCTGGCTGAT GTGGAAAGCA AAGGGCACAG TGGGATTTGA AAACCAGATC    1440

AACAAATGCC TGGAACTGGC TGAATACCTC TATGCCAAGA TTAAAAACAG AGAAGAATTT    1500

GAGATGGTTT TCAATGGCGA GCCTGAGCAC ACAAACGTCT GTTTTTGGTA TATTCCACAA    1560

AGCCTCAGGG GTGTGCCAGA CAGCCCTCAA CGACGGGAAA AGCTACACAA GGTGGCTCCA    1620

AAAATCAAAG CCCTGATGAT GGAGTCAGGT ACGACCATGG TTGGCTACCA GCCCCAAGGG    1680

GACAAGGCCA ACTTCTTCCG GATGGTCATC TCCAACCCAG CCGCTACCCA GTCTGACATT    1740

GACTTCCTCA TTGAGGAGAT AGAAAGACTG GGCCAGGATC TGTAA                    1785
```

(2) INFORMATION FOR SEQ ID NO:2:

(i) SEQUENCE CHARACTERISTICS:
        (A) LENGTH: 594 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Met Ala Ser Ser Thr Pro Ser Ser Ala Thr Ser Ser Asn Ala Gly
 1               5                  10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
                35                  40                  45

Gly Phe Leu Gln Arg Thr Asn Ser Leu Glu Glu Lys Ser Arg Leu Val
         50                  55                  60
```

```
Ser Ala Phe Lys Glu Arg Gln Ser Ser Lys Asn Leu Leu Ser Cys Glu
 65                  70                  75                  80

Asn Ser Asp Arg Asp Ala Arg Phe Arg Thr Glu Thr Asp Phe Ser
                 85                  90                  95

Asn Leu Phe Ala Arg Asp Leu Leu Pro Ala Lys Asn Gly Glu Gln
                100                 105                 110

Thr Val Gln Phe Leu Leu Glu Val Val Asp Ile Leu Leu Asn Tyr Val
            115                 120                 125

Arg Lys Thr Phe Asp Arg Ser Thr Lys Val Leu Asp Phe His His Xaa
        130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
        290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Xaa Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Leu Gln Cys Gly Arg His Val Asp Val Phe Lys Leu
450                 455                 460

Trp Leu Met Trp Arg Ala Lys Gly Thr Thr Gly Phe Glu Ala His Ile
465                 470                 475                 480

Asp Lys Cys Leu Glu Leu Ala Glu Tyr Leu Tyr Asn Ile Ile Lys Asn
```

```
                485               490               495
Arg Glu Gly Tyr Glu Met Val Phe Asp Gly Lys Pro Gln His Thr Asn
            500             505             510
Val Cys Phe Trp Phe Val Pro Pro Ser Leu Arg Val Leu Glu Asp Asn
        515             520             525
Glu Glu Arg Met Ser Arg Leu Ser Lys Val Ala Pro Val Ile Lys Ala
    530             535             540
Arg Met Met Glu Tyr Gly Thr Thr Met Val Ser Tyr Gln Pro Leu Gly
545             550             555             560
Asp Lys Val Asn Phe Phe Arg Met Val Ile Ser Asn Pro Ala Ala Thr
                565             570             575
His Gln Asp Ile Asp Phe Leu Ile Glu Glu Ile Glu Arg Leu Gly Gln
            580             585             590
Asp Leu
```

(2) INFORMATION FOR SEQ ID NO:3:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:3:

```
ATGGCGTCTT CGACCCCATC TTCGTCCGCA ACCTCCTCGA ACGCGGGAGC GGACCCCAAT    60
ACCACTAACC TGCGCCCCAC AACGTACGAT ACCTGGTGCG GCGTGGCCCA TGGATGCACC   120
AGAAAACTGG GGCTCAAGAT CTGCGGCTTC TTGCAAAGGA CCAACAGCCT GGAAGAGAAG   180
AGTCGCCTTG TGAGTGCCTT CAAGGAGAGG CAATCCTCCA AGAACCTGCT TTCCTGTGAA   240
AACAGCGACC GGGATGCCCG CTTCCGGCGC ACAGAGACTG ACTTCTCTAA TCTGTTTGCT   300
AGAGATCTGC TTCCGGCTAA GAACGGTGAG GAGCAAACCG TGCAATTCCT CCTGGAAGTG   360
GTGGACATAC TCCTCAACTA TGTCCGCAAG ACATTTGATC GCTCCACCAA GGTGCTGGAC   420
TTTCATCACC CACACCAGTT GCTGGAAGGC ATGGAGGGCT TCAACTTGGA GCTCTCTGAC   480
CACCCCGAGT CCCTGGAGCA GATCCTGGTT GACTGCAGAG ACACCTTGAA GTATGGGGTT   540
CGCACAGGTC ATCCTCGATT TTTCAACCAG CTCTCCACTG GATTGGATAT TATTGGCCTA   600
GCTGGAGAAT GGCTGACATC AACGGCCAAT ACCAACATGT TTACATATGA AATTGCACCA   660
GTGTTTGTCC TCATGGAACA AATAACACTT AAGAAGATGA GAGAGATAGT TGGATGGTCA   720
AGTAAAGATG GTGATGGGAT ATTTTCTCCT GGGGGAGCCA TATCCAACAT GTACAGCATC   780
ATGGCTGCTC GCTACAAGTA CTTCCCGGAA GTTAAGACAA AGGGCATGGC GGCTGTGCCT   840
AAACTGGTCC TCTTCACCTC AGAACAGAGT CACTATTCCA TAAAGAAAGC TGGGGCTGCA   900
CTTGGCTTTG GAACTGACAA TGTGATTTTG ATAAAGTGCA ATGAAAGGGG GAAAATAATT   960
CCAGCTGATT TGAGGCAAA AATTCTTGAA GCCAAACAGA AGGGATATGT TCCCTTTTAT  1020
GTCAATGCAA CTGCTGGCAC GACTGTTTAT GGAGCTTTTG ATCCGATACA AGAGATTGCA  1080
GATATATGTG AGAAATATAA CCTTTGGTTG CATGTCGATG CTGCCTGGGG AGGTGGGCTG  1140
CTCATGTCCA GGAAGCACCG CCATAAACTC AACGGCATAG AAAGGGCCAA CTCAGTCACC  1200
TGGAACCCTC ACAAGATGAT GGGCGTGCTG TTGCAGTGCT CTGCCATTCT CGTCAAGGAA  1260
AAGGGTATAC TCCAAGGATG CAACCAGATG TGTGCAGGAT ACCTCTTCCA GCCAGACAAG  1320
```

```
CAGTATGATG TCTCCTATGA CACGGGAGAC AAGGCCTTGC AGTGTGGACG CCACGTCGAT    1380

GTCTTTAAAT TATGGCTCAT GTGGAGAGCA AAGGGGACTA CTGGATTTGA AGCTCACATT    1440

GATAAGTGTT TGGAGCTGGC AGAGTATTTA TACAATATCA TTAAAAACCG AGAAGGATAT    1500

GAAATGGTGT TCGATGGGAA GCCTCAGCAC ACAAATGTCT GCTTCTGGTT TGTACCTCCT    1560

AGTTTGCGAG TTCTGGAAGA CAATGAAGAG AGAATGAGCC GCCTCTCAAA GGTGGCGCCA    1620

GTGATTAAAG CCAGAATGAT GGAGTATGGG ACCACAATGG TCAGCTACCA ACCCTTAGGA    1680

GATAAGGTCA ACTTCTTCCG CATGGTCATC TCAAACCCTG CAGCAACTCA CCAAGACATT    1740

GACTTCCTCA TTGAAGAAAT CGAACGCCTG GGACAAGATT TGTAA                    1785
```

(2) INFORMATION FOR SEQ ID NO:4:

(i) SEQUENCE CHARACTERISTICS:
       (A) LENGTH: 594 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:4:

```
Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
210                 215                 220

Leu Glu Tyr Val Thr Leu Lys Lys Met Arg Glu Ile Ile Gly Trp Pro
225                 230                 235                 240

Gly Gly Ser Gly Asp Gly Ile Phe Ser Pro Gly Gly Ala Ile Ser Asn
                245                 250                 255

Met Tyr Ala Met Leu Ile Ala Arg Tyr Lys Met Phe Pro Glu Val Lys
            260                 265                 270
```

Glu Lys Gly Met Ala Ala Val Pro Arg Leu Ile Ala Phe Thr Ser Glu
            275                 280                 285

His Ser His Phe Ser Leu Lys Lys Gly Ala Ala Leu Gly Ile Gly
    290                 295                 300

Thr Asp Ser Val Ile Leu Ile Lys Cys Asp Glu Arg Gly Lys Met Ile
305                 310                 315                 320

Pro Ser Asp Leu Glu Arg Arg Ile Leu Glu Val Lys Gln Lys Gly Phe
                325                 330                 335

Val Pro Phe Leu Val Ser Ala Thr Ala Gly Thr Thr Val Tyr Gly Ala
            340                 345                 350

Phe Asp Pro Leu Leu Ala Val Ala Asp Ile Cys Lys Lys Tyr Lys Ile
            355                 360                 365

Trp Met His Val Asp Ala Ala Trp Gly Gly Gly Leu Leu Met Ser Arg
    370                 375                 380

Lys His Lys Trp Lys Leu Asn Gly Val Glu Arg Ala Asn Ser Val Thr
385                 390                 395                 400

Trp Asn Pro His Lys Met Met Gly Val Pro Leu Gln Cys Ser Ala Leu
                405                 410                 415

Leu Val Arg Glu Glu Gly Leu Met Gln Ser Cys Asn Gln Met His Ala
            420                 425                 430

Ser Tyr Leu Phe Gln Gln Asp Lys His Tyr Asp Leu Ser Tyr Asp Thr
            435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
            515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu (2) INFORMATION FOR SEQ ID NO:5:

(i) SEQUENCE CHARACTERISTICS:
        (A) LENGTH: 166 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Val Pro Arg Leu Ile Ala Phe Thr Ser Glu His Ser His Phe Ser Leu
1               5                   10                  15

-continued

```
Lys Lys Gly Ala Ala Ala Leu Gly Ile Gly Thr Asp Ser Val Ile Leu
        20                  25                  30

Ile Lys Cys Asp Glu Arg Gly Lys Met Ile Pro Ser Asp Leu Glu Arg
        35                  40                  45

Arg Ile Leu Glu Val Lys Gln Lys Gly Phe Val Pro Phe Leu Val Ser
    50                  55                  60

Ala Thr Ala Gly Thr Thr Val Tyr Gly Ala Phe Asp Pro Leu Leu Ala
65                  70                  75                  80

Val Ala Asp Ile Cys Lys Lys Tyr Lys Ile Trp Met His Val Asp Ala
                85                  90                  95

Ala Trp Gly Gly Gly Leu Leu Met Ser Arg Lys His Lys Trp Lys Leu
            100                 105                 110

Asn Gly Val Glu Arg Ala Asn Ser Val Thr Trp Asn Pro His Lys Met
        115                 120                 125

Met Gly Val Pro Leu Gln Cys Ser Ala Leu Leu Val Arg Glu Glu Gly
    130                 135                 140

Leu Met Gln Ser Cys Asn Gln Met His Ala Ser Tyr Leu Phe Gln Gln
145                 150                 155                 160

Asp Lys His Tyr Asp Leu
                165

(2) INFORMATION FOR SEQ ID NO:6:

(i) SEQUENCE CHARACTERISTICS:
        (A) LENGTH: 120 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Asp Val Phe Lys Leu Trp Leu Met Trp Arg Ala Lys Gly Thr Thr Gly
1               5                   10                  15

Phe Glu Ala His Ile Asp Lys Cys Leu Glu Leu Ala Glu Tyr Leu Tyr
            20                  25                  30

Asn Ile Ile Lys Asn Arg Glu Gly Tyr Glu Met Val Phe Asp Gly Lys
        35                  40                  45

Pro Gln His Thr Asn Val Cys Phe Trp Phe Val Pro Pro Ser Leu Arg
    50                  55                  60

Val Leu Glu Asp Asn Glu Glu Arg Met Ser Arg Leu Ser Lys Val Ala
65                  70                  75                  80

Pro Val Ile Lys Ala Arg Met Met Glu Tyr Gly Thr Thr Met Val Ser
                85                  90                  95

Tyr Gln Pro Leu Gly Asp Lys Val Asn Phe Phe Arg Met Val Ile Ser
            100                 105                 110

Asn Pro Ala Ala Thr His Gln Asp
        115                 120
```

INSULIN-DEPENDENT DIABETES MELLITUS-SPECIFIC CHIMERIC POLYPEPTIDES

This application is a Divisional Application of, and claims the benefit of, application Ser. No. 08/592,696, filed Jan. 26, 1996, which status is now U.S. Pat. No. 5,821,334, which application is hereby incorporated herein by reference.

This invention was made with government support under an RO1 grant awarded by the National Institutes of Health and under Veteran's Affairs Administration Research Service Career Development Award and Merit Review Award. The government may have certain rights in the invention.

BACKGROUND OF THE INVENTION

1. Field of the Invention

The present invention provides chimeric polypeptides having one or more glutamic acid decarboxylase (GAD) 65 epitopes, wherein the chimeric polypeptides can specifically bind a GAD antibody present in serum from a subject having insulin-dependent diabetes mellitus (IDDM, also referred to as type I diabetes). The chimeric polypeptides can be used to detect individuals having new-onset diabetes, who are in the prediabetic stage of type I diabetes or to classify the type of diabetes in an individual as type I.

2. Background Art

Insulin-dependent diabetes mellitus (IDDM) (also known as type 1 diabetes) primarily afflicts young people. Although insulin is available for treatment, the several-fold increased morbidity and mortality associated with this disease require the development of early diagnostic and preventive methods. The destruction of pancreatic β-cells (which are the insulin-secreting cells of the islets of Langerhans) that precedes the clinical onset of IDDM, is mediated by autoimmnuune mechanisms. Among the most thoroughly studied autoimmune abnormalities associated with the disease is the high incidence of circulating β-cell specific autoantibodies at the time of diagnosis. Family studies have shown that the autoantibodies appear prior to overt IDDM by a number of years, suggesting a long prodromal period of humoral autoimmunity before clinical symptoms emerge. The family studies have also documented a slow, progressive loss of insulin response to intravenous glucose in the years preceding diagnosis. The presence of β-cell specific autoantibodies in the prediabetic period is likely to reflect the ongoing autoimmune process, one that eventually leads to critical β-cell depletion and insulin dependency. It has been estimated that only 10% of the total β-cell mass remains at the time of clinical onset.

A major autoantigen for both humoral and cellular autoimmmunity in insulin-dependent diabetes mellitus (EDM) is glutamic acid decarboxylase (GAD) (Baekkeskov et al. (1990), *Nature* 347:151–156; Solimena (1991), *Trends in Neurosciences* 14:452–457; Clare-Salzer et al. (1992), *Diabetes Care* 15:132–135). The possible role of GAD as the primary autoantigen in IDDM has been suggested by recent demonstrations of cellular autoimmunity directed at GAD in IDDM (Honeyman et al. (1993), *J. Exp. Med.* 177:535–540; Atkinson et al. (1992), *Lancet* 339:458–459) as well as autoimmunity directed at GAD in an animal model of IDDM (Kaufman et al. (1993), *Nature* 366:69–72; Tisch et al. (1993), *Nature* 366:72–75). GAD autoantibodies are an important marker of the autoimmune process of IDDM since they are present in the majority of individuals with new-onset diabetes and in individuals in the prediabetic stage of the disease (Hagopian et al. (1993), *J. Clin. Invest.* 91:368–374; Rowley et al. (1992) *Diabetes* 41:548–551; De Aizpurua et al. (1992), *Proc. Natl. Acad. Sci. USA* 89:9841–9845).

GAD is the biosynthetic enzyme for the inhibitory neurotransritter γ-amino butyric acid (Erlander et al. (1991), *Neurochem. Res.* 16:215–226). Two isoforms, $GAD_{65}$ (65 kDa) and $GAD_{67}$ (67 kDa) are the products of two separate genes, are highly homologous, and differ mostly in the amino terminal-third of the protein (Erlander et al. (1991); Bu et al. (1992), *Proc. Natl. Acad. Sci. USA* 89:2115–2119; Christgau et al. (1991), *J. Biol. Chem.* 266:21257–21269). The respective cDNAs for $GAD_{65}$ and $GAD_{67}$ are identical in the brain and islet (Clare-Salzer et al. (1992), *Diabetes Care* 15:132–135; Giorda et al. (1991), *Lancet* 338:1469–1470; Kelly et al. (1991), *Lancet* 338:1468–1469; Karlsen et al. (1991), *Proc. Nat. Acad. Sci. USA* 88:8337–8341; Cram et al. (1991), *Biochem. Biophys. Res. Commun.* 176:1239–1244; Michelson et al. (1991), *Proc. Natl. Acad. Sci. USA* 88:8754–8758). In the human, $GAD_{65}$ is the predominant form expressed in the islet, whereas both $GAD_{65}$ and $GAD_{67}$ are found in rat islets (Velloso et al. (1993), *Diabetologia* 36:39–46; Kim et al. (1993), *Diabetes* 42:1799–1808). Mouse islets contain little, if any, $GAD_{65}$ (Velloso et al. (1993); Kim et al. (1993).

Antibodies against GAD, originally detected by Baekkeskov et al. (1993), are found in the majority of individuals with preclinical and new-onset type I diabetes and have been detected utilizing recombinant GAD and porcine brain GAD (Velloso et al. (1993) *J. Clin. Invest.* 91:2084–2090; Hagopian et al. (1993) *J. Clin. Invest.* 91:368–374; Karlsen et al. (1992) *Diabetes* 41:1355–1359; Christie et al. (1992) *Diabetologia* 35:380–384; Rowley et al. (1992), *Diabetes* 41:548–551; Clare-Salzler et al. (1992), *Diabetes Care* 15:132–135; DeAizpurua et al. (1992), *Diabetes* 41:1182–1187; DeAizpurua et al. (1992), *Proc. Natl. Acad. Sci. USA* 89:9841–9845). Some ICA sera react with $GAD_{65}$ and $GAD_{67}$, but $GAD_{65}$ is the predominant autoantigen (Velloso et al. (1993); Hagopian et al. (1993), *Diabetes* 42:631–636). An initial report mapped the reactivity of four ICA sera to the middle and COOH-terminal of $GAD_{65}$ Kaufman et al. (1992) *J. Clin. Invest.* 89:283–292). A recent study using a series of GAD-directed monoclonal antibodies from a single patient with type I diabetes has detected at least two distinct epitopes, one that is linear in nature and one that is dependent on protein conformation (Richter et al. (1993), *Proc. Natl. Acad. Sci. USA* 90:2832–2836; Richter et al. (1992), *Proc. Natl. Acad. Sci. USA* 89:8467–8471).

$GAD_{67}$ and $GAD_{65}$ are highly diverse in the first 95 amino acids but share significant (approx. 75%) homology in the rest of the molecule. Both have a proteolytic hot spot 80–90 amino acids from the N-terminus (Christgau et al. (1991), *J. Biol. Chem.* 266:21257–21264; Christgau et al. (1992), *J. Cell Biol.* 118:309–320) (incorporated by reference in their entirety for all purposes), which may represent a domain boundary. The N-terminal domain harbors the post-translational modifications which result in anchoring of $GAD_{65}$ to the membrane of synaptic vesicles and control the distinct subcellular localization of this protein.

In brain tissue, both $GAD_{65}$ and $GAD_{67}$ are produced (Bu et al. (1992), *Proc. Natl. Acad. Sci. USA* 89:2115–2119; Kaufman et al. (1986) *Science* 232:1138–1140; Chang & Gottlieb (1988), *J. Neurosci.* 8:2123–2130). Some species express both GAD proteins in their pancreatic islets. However, in human islets only $GAD_{65}$ is expressed (Karlsen et al. (1991), *Proc. Natl. Acad. Sci. (USA)* 88:8337–8341; Karlsen et al. (1992), *Diabetes* 41:1355–1359). Immunogenic crossreactivity between isolates of $GAD_{65}$ and $GAD_{67}$ from different vertebrate species indicates a high degree of conservation of antigenic determinants from rodents to humans (Legay et al. (1986), *J. Neurochem.* 46:1478–1486). Consistent with this observation, human $GAD_{65}$ and $GAD_{67}$ polypeptides share more than 80% amino-acid sequence identity with cognate polypeptides in other mammals. Bu et al., supra.

GAD autoantibodies that bind the intact, full length GAD65 protein are also found in some individuals without IDDM including individuals with stiff-man syndrome (SMS), polyglandular failure type I, and individuals who have a restricted or beta-cell specific islet cell autoantibody (ICA) pattern (Solimena et al. (1991), *Trends in Neurosciences* 14:452–457; Genovese et al. (1992), *Diabetologia* 35:385–388; Gianani et al. (1992), *Diabetes* 41:347–353; Bjork et al. (1994), *Diabetes* 43:161–165). These individuals have a low risk of developing IDDM. Differences and heterogeneity in the GAD autoantibody profile between these non-diabetic individuals and those with IDDM suggest that disease-specific epitopes may exist (Bjork et al. (1994), *Diabetes* 43:161–165; Butler et al. (1993), *J. Exp. Med.* 178:2097–2106; Kim et al. (1994), *J. Exp. Med.* 180:595–606; Ujihara et al. (1994), *Diabetes* 43:968–975). For example, SMS sera bind GAD protein fagments and denatured GAD protein utilized in immunoblotting (Baekkeskov et al. (1990), *Nature* 347:151–156; Butler et al. (1993), *J. Exp. Med.* 178:2097–2106; Kim et al. (1994). *J Exp. Med.* 180:595–606).

In contrast, GAD antibodies in IDDM do not bind denatured GAD protein, GAD fragments, or GAD peptides which implies that these GAD antibodies bind an epitope dependent on protein conformation (Baekkeskov et al. (1990), *Nature* 347:151–156; Ujihara et al. (1994), *Diabetes* 43:968–975; Richter et al. (1993), *Proc Natl Acad Sci USA* 90:2832–2836). The COOH-terminal two-thirds of the GAD 65 protein contains the region targeted in IDDM, but when smaller fagments of GAD 65 protein are used, most binding by IDDM sera is lost (Ujihara et al. (1994), *Diabetes* 43:968–975; Richter et al. (1993), *Proc Natl Acad Sci USA* 90:2832–2836). Hence, further localization of the IDDM epitopes is not possible with the methodology used to map GAD epitopes targeted by SMS or restricted ICA sera. Furthermore, when native, full length GAD65 is used, some sera from individuals without IDDM who have, for example, SMS, polyglandular renal failure type I, or a restricted or βcell-specific ICA pattern bind the GAD65 protein causing false positives for diagnosis of IDDM.

The present invention overcomes these experimental limitations in localizing IDDM-related GAD epitopes by designing recombinant GAD proteins that maintain the conformation of the GAD protein. By exchanging regions of the GAD 65 and GAD 67 cDNAs, we created chimeric GAD polypeptides and determined the binding of IDDM antibodies to different regions of the GAD 65 protein. These chimeric polypeptides utilize one or more epitopes of GAD 65 such that the chimeric protein can bind IDDM sera. The chimeric polypeptides of the present invention provide more specific binding for IDDM GAD autoantibodies than intact GAD65, and produce fewer false positives for binding of IDDM-specific GAD autoantibodies and, thus, provide a more useful diagnostic polypeptide.

SUMMARY OF THE INVENTION

The present invention provides a chimeric polypeptide comprising an epitope of GAD65 protein and a structural region comprising a polypeptide of the GAD family, wherein the chimeric polypeptide is a more specific diagnostic for insulin dependent diabetes mellitus than intact GAD65 and produces fewer false positives than intact GAD65.

The present invention further provides a chimeric polypeptide comprising an epitope of GAD65 inserted into GAD67 wherein the GAD65 epitope replaces amino acids of GAD67 corresponding to amino acids of the GAD65 epitope and wherein the chimeric polypeptide is a more specific diagnostic for insulin dependent diabetes mellitus than intact GAD65 and produces fewer false positives than intact GAD65.

The present invention further provides a method of screening for the presence of GAD antibodies in a sample comprising contacting the sample with the chimeric polypeptide of claim 1 and detecting binding between an antibody in the sample and the chimeric polypeptide, the detection of binding indicating the presence of GAD antibodies in the sample.

The present invention further provides a method of screening a subject for risk of developing IDDM, comprising contacting the chimeric polypeptide of claim 1 with a biological sample containing antibodies from the subject and detecting binding between an antibody in the biological sample and the chimeric polypeptide, the detection of binding indicating the subject is at risk of developing IDDM.

The present invention further provides a method of determining if a subject having a type of diabetes has type I diabetes, comprising contacting the chimeric polypeptide of claim 1 with a biological sample containing antibodies from the subject and detecting binding between an antibody in the biological sample and the chimeric polypeptide, the detection of binding indicating the type of diabetes in the subject is type I diabetes.

BRIEEF DESCRIPTION OF THE DRAWINGS

FIG. 1 provides a schematic drawing of (A) unaltered GAD 65 and GAD 67, (B) chimeric proteins GAD 67 (1–230/GAD 65 (221–442)/GAD67 (452–594), and GAD 67 (14–51)/GAD 65 (443–585), and (C) a chimeric protein template depicting regions that can be modified as hatched bars. In all drawings, solid white bars denote GAD 65 sequences and solid black bars denote GAD 67 sequences. The nomenclature for GAD protein fragments or chimeric proteins utilizes the following pattern: GAD 65 or 67 (number of amino acids of that GAD species present in the GAD fragment). For example, a GAD 65 fragment containing the first 195 amino acids is referred to as GAD 65 (1–195). If no amino acid number is shown in parentheses, then the protein is full-length GAD 65 (amino acids 1–585) or GAD 67 (amino acids 1–594). The junction of chimeric proteins is noted by the (/) symbol.

DESCRIPTION OF PREFERRED EMBODIMENTS

Figure 1:
Figure 1:
Figure 1:
Figure 1:
Figure 1:
Figure 1:
Figure 1:

The present invention may be understood more readily by reference to the following detailed description of preferred embodiments of the inventions and the Examples included therein.

The present invention provides a chimeric polypeptide comprising an epitope of GAD65 protein and a structural region comprising a polypeptide of the GAD family, wherein the chimeric polypeptide is a more specific diagnostic for insulin dependent diabetes meditus than intact GAD65 and produces fewer false positives than intact GAD65.

"Insulin dependent diabetes mellitus" (IDDM) and "type 1 diabetes" are used interchangeably herein.

As used herein, an epitope of GAD65 protein is a region of the GAD65 protein that can specifically bind a GAD antibody. The GAD antibody can be a known antibody, such as monoclonal antibodies that react with GAD. For example, monoclonal antibodies GAD1, GAD6, or monoclonal islet cell antibody (MICA) 1 and MICA 3 (isolated from a single patient with IDDM (Richter et al. *Proc. Natl. Acad. Sci. USA* 90:2832–2836 (1993)) can be used. Preferably, however, an epitope of GAD65 is determined by its ability to specifically bind an antibody in serum from an individual with IDDM. Therefore, a preferable method of determining if any selected polypeptide, chimeric polypeptide or fragment thereof contains an epitope of GAD65 is to contact the polypeptide, chimeric polypeptide or fragment with serum from one or more individuals diagnosed by conventional methods as having IDDM and determining whether a reaction occurs with the serum, a reaction indicating that a GAD65 epitope is present. Such methods of determining antibody-antigen reactions are exemplified herein and, further, are well-known in the art (see, e.g., Harlow and Lane, *Antibodies: A Laboratory Manual*, Cold Spring Harbor Laboratory, Cold Spring Harbor, N.Y., 1988). Epitopes can be further delineated, if desired, by this method. Epitopes can be further delineated also by constructing additional chimeric proteins, as taught herein for the construction, and performning the assay described above. More than one epitope can be utilized, as desired, in contiguous array or separated within the chimeric protein, as further described herein.

By "GAD65" and "GAD67" is meant to include any mammalian GAD65 or GAD 67 polypeptide, respectively, since immunogenic cross-reactivity between isolates of GAD65 and GAD67 from different vertebrate species indicates a high degree of conservation of antigenic determinants from rodents to humans (Legay et al. *J. Neurochem.* 46: 1478–1486 (1986)). Examples of such mammals can include human, nonhuman primate, cow, rabbit, dog, cat, pig, rat, mouse and hamster. Preferable mammalian GAD 65 epitopes can be derived from human, bovine, pig or rat GAD 65, shown to react with human antibodies. The cDNAs encoding human brain GAD65 and GAD67 have been cloned and the sequence determined. (Bu et al. *Proc. Natl. Acad. Sci. USA* 89: 2115–2119 (1992)). DNA sequences have also been determined for human pancreatic beta cell GAD65 (Karlsen et al. *Proc. Natl. Acad. Sci. USA* 88: 8337–8341(1991)), rat brain GAD65 and GAD67 (Erlander et al. *Neuron* 7:91–100 (1991)); Julien et al. *J.Neurochem.* 54:703–705 (1990)), and rat beta cell GAD65 (Michelson et al., *Proc. Natl. Acad. Sci. USA* 88: 8754–8758 (1991)). Furthermore, any chimeric polypeptide according to this invention can have within it sequences derived from more than one mammal. For example, the GAD sequences present in SEQ ID NOs: 1–6 are derived from rat GAD65 and human GAD67.

By a "structural region" of a chimeric polypeptide as used herein is meant a region utilized for conformation and or backbone structure of the chimeric protein rather than for immunoreactivity. Typically, the structural region from GAD67 will correspond to structural regions from GAD family proteins. However, structural region is used herein to refer to the region's function in the chimeric polypeptides. Structural regions can have one or more epitopes that bind a GAD autoantibody present in serum from a subject with IDDM, but should not contain regions that non-specifically bind an antibody present in serum from a subject with IDDM or that bind a non-GAD antibody that can be present in serum from a subject with IDDM. The structural region can be used to achieve the proper tertiary placement of the GAD65 epitope for recognition by a GAD autoantibody present in serum from a subject with IDDM. The structural region preferably includes a region of GAD67. Sequences of amino acids from GAD67 can be placed, if desired, in the chimeric polypeptide in the corresponding region of the chimeric protein as those sequences present in the native GAD67 protein. The region of GAD67 in the structural region of the chimeric protein can range from about 10 consecutive amino acids to a maximum size limited only by the overall size and conformation of the chimeric protein such that the GAD65 epitopes can react with the IDDM serum, as described herein. Preferably the GAD67 region is from about 15 consecutive amino acids to about 594 amino acids in size. More than one region of GAD67 can be utilized in a chimeric protein, and the regions can be contiguous within the chimeric polypeptide or scattered throughout the chimeric polypeptide. Additionally, the structural region of a chimeric polypeptide of this invention can comprise polypeptide regions from other proteins, as described herein.

The GAD family includes proteins having glutamic acid decarboxylase activity and which are approximately the size of GAD65 (585 amino acids in length), i.e., about 400 to about 800 amino acids in length. Examples of such proteins include GAD67, a reported brain additional GAD protein (Nathan, B. *J.Biol.Chem.* 269:7249–7254 (1994); Nathan, B. *Proc. Natl. Acad. Sci.* 94:242–246 (1994)), *Drosophila* GAD (Jackson, F. *J.Neurochem.* 54:1068–1078 (1990)), and *E. coli* GAD (Maras, B. *Eur.J.Biochem.* 24:93–98 (1992)).

The term "polypeptide" refers to a polymer of amino acids and includes full-length proteins and fragments thereof. As used in the specification and in the claims, "a" can mean one or more, depending upon the context in which it is used.

An epitope of GAD65 can comprise two or more regions of GAD65 separated by substituted amino acids to retain the native conformation of the epitope. For example, GAD65 amino acids 443–513 and/or 528–585 can comprise an epitope. Preferably, these two example regions are in a chimeric protein separated by about 10 to about 20, and preferably, about 15, amino acids, thus providing about the same conformation of these two regions of the epitope. Amino acids in the separating region should preferably be neutral substitutions of the amino acids present in the GAD 65 protein at positions 514–527. Substitutions can be selected by known parameters to be neutral (see, e.g., Robinson W E Jr, and Mitchell W M., AIDS 4:S151–S162 (1990)), and resulting chimeric proteins can readily be tested for function by reacting them with IDDM serum, as described herein.

Another useful epitope is GAD65 amino acids 270–435. Yet another useful epitope is GAD65 amino acids 451–570. GAD65 sequences 221–442 and 451–585 can also be placed into a chimeric polypeptide to form a useful chimeric polypeptide.

The amino-terminal 230 amino acids of GAD65 or GAD67 are not necessary for a chimeric protein to retain the function of immunoreactivity with IDDM serum. Thus, for example, another useful chimeric protein is a chimeric protein comprising amino acids 231–585 of the chimeric protein having the amino acid sequence set forth in SEQ ID NO:2, and another is a chimeric protein comprising amino acids 231–585 of the chimeric protein having the amino acid sequence set forth in SEQ ID NO:4. Additional amino acids can readily be fused to the ends of these two examples of chimeric proteins, preferably at the amino-terminal end.

Additional amino acids can be present in the chimeric proteins of the present invention. These additional amino acids can be modifications to or substitutions of GAD amino acid sequences or can comprise additional regions of amino acid sequence, for example, regions derived from non-GAD proteins. Such amino acids should not have an epitope that reacts non-specifically with IDDM serum or that binds a non-GAD antibody that can be present in serum from a subject with IDDM, to avoid false positive results. In general, it is preferable for any chimeric protein of this invention to be of a size to maintain conformation that places the epitope(s) in a position wherein it can be recognized by a GAD autoantibody in IDDM serum. Thus the size of the chimeric protein can be somewhat similar to that of the native GAD65 and GAD67. Thus it is preferable that the chimeric proteins be from about 1000 amino acids to about 350 amino acids, more preferably about 800 amino acids to about 500 amino acids, and more preferably about 600 amino acids to about 350 amino acids.

FIG. 1(C) depicts a general template for construction of chimeric polypeptides of this invention, with the GAD65 sequences and their general placement within the chimeric polypeptide denoted. Generally, the placement of GAD65 epitope(s) can be relative to the carboxy terminus of the polypeptide, in particular since, in native GAD65 or in chimeric polypeptides having GAD65 or GAD67 sequences at the amino terminal end, the amino-terminal 230 amino acids are found not to be necessary for immuno-reactivity of the polypeptide, and therefore, can be completely removed (e.g., other useful chimeric proteins include the chimeric polypeptide having the amino acid sequence set forth in SEQ ID NO:2 with the amino-terminal 230 amino acids removed and the chimeric polypeptide having the amino acid sequence set forthin SEQ. ID No. 4 with the animo-terminal 230 amino acids removed). Regarding the general template, for example, in a chimeric polypeptide of a size about 600 amino acids, a GAD65 epitope can be placed such that its N-terminal end is about 380 amino acids from the carboxy terminus, about 350 amino acids from the carboxy terminus, at about 150 amino acids from the carboxy terminus, or at about 75 amino acids from the carboxy terminus. The C-terminal end of a GAD65 epitope for example, can be at the C-terminal end of the chimeric polypeptide, about 57 amino acids from the carboxy terminus, about 142 amino acids from the carboxy terminus, or about 72 amino acids from the carboxy terminus. However, as described herein, the GAD65 epitopes can be placed at any position that allows binding of the epitope to the antibody in IDDM serum.

Additional regions of amino acid sequence can be derived from any selected protein (denoted "Protein X" in FIG. 1(C)). In general, these regions are selected from proteins that will provide the proper conformation to the chimeric polypeptide to allow binding of the GAD65 epitope(s) to the corresponding autoantibody in IDDM serum. For example, regions selected from GAD family proteins, can readily be utilized in a chimeric polypeptide.

The chimeric polypeptides of the present invention provide a more specific diagnostic for IDDM than intact GAD65. By intact GAD 65 is meant the full length GAD65 protein. Greater specificity as a diagnostic can readily be determined by individually contacting the intact GAD65 and the chimeric polypeptide with control serum and with serum from an IDDM subject and determining the realitive speci-ficity of the chimeric polypeptide to the GAD65 by accuracy of detection of binding only IDDM sera. The chimeric polypeptides of this invention produce fewer false positives for the presence of IDDM-specific GAD autoantibodies than intact GAD65. The ability to produce fewer false positives is readily determined by contradicting the chimeric polypeptides with a panel of control sera (non-IDDM) and sera from individuals having IDDM. Levels of binding GAD autoantibodies and/or simple detection of any binding can be determined. False positives are detection of binding in a control sample.

As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The polypeptides may comprise one or more selected antigenic determinants of human islet GAD, possess catalytic activity exhibited by native GAD protein or alternatively lack such activity, mimic GAD binding regions, or the like.

The present invention further provides a nucleic acid encoding the chimeric polypeptides of the present invention. For example, the nucleic acid set forth herein as SEQ ID NO: 1 provides a nucleotide sequence for a nucleic acid that encodes the GAD67 (1–230)/GAD65 (221–442)/GAD67 (542–594) chimeric polypeptide set forth in SEQ ID NO: 2. Another example of such a nucleic acid set forth herein as SEQ ID NO: 3 provides a nucleotide sequence for a nucleic acid that encodes the GAD67 (1–451)/GAD65 (443–585) chimeric polypeptide set forth in SEQ ID NO: 4. Additional nucleic acids encoding these chimeric proteins can readily be made, utilizing the degeneracy of the genetic code. Additionally, a nucleic acid encoding any selected chimeric protein can readily be made, based upon the genetic code, as known in the art. Nucleic acids can be obtained by any of several means known in the art. For example, cDNAs can be isolated from a library using a probe derived from the present nucleic acids or polypeptides, or nucleic acids can be directly synthesized mechanically.

The present method additionally provides a method of screening for the presence of GAD antibodies in a sample comprising (a) contacting the sample with a chimeric polypeptide comprising an epitope of GAD65 protein and a structural region comprising a polypeptide of the GAD family, wherein the chimeric polypeptide is a more specific diagnostic for IDDM than intact GAD65 and produces fewer false positives than intact GAD65, and (b) detecting binding between an antibody in the sample and the chimeric polypeptide, the detection of binding indicating the presence of GAD antibodies in the sample. A sample can include any sample in which GAD antibodies may be present. Typically, the sample will be a biological sample, which, as used herein, can include any sample from a subject in which antibodies generally can be detected, such as blood, serum and amniotic fluid. In any assay of the present invention, binding between an antibody in a sample and a chimeric polypeptide can be readily detected using any known means for detecting such binding, as exemplified in the examples herein.

As will be recognized by those skilled in the art, numerous types of immunoassays are available for use in the present invention to detect binding between an antibody and a chimeric polypeptide of this invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988).

The present method additionally provides a method of screening a subject for risk of developing IDDM, comprising (a) contacting a chimeric polypeptide comprising an epitope of GAD65 protein and a structural region comprising a polypeptide of the GAD family, wherein the chimeric polypeptide is a more specific diagnostic for IDDM than intact GAD65 and produces fewer false positives than intact GAD65, with a biological sample from the subject and (b) detecting binding between an antibody in the sample and the chimeric polypeptide, the detection of binding indicating the subject is at risk of developing IDDM. GAD antibodies, as exemplified by the examples herein, are present in the majority of individuals in the prediabetic stage of the disease. Thus the detection of binding indicates a subject at risk of developing IDDM. Early detection can affect the course of therapy for the individual, and blood levels of insulin can be closely monitored once GAD antibodies are detected. A preferable chimeric polypeptide has a GAD 65 epitope of GAD65 amino acids 270–435 and/or GAD65 amino acids 451–570. The epitope, for example, can have the amino acid sequence set forth in SEQ ID NO: 5 or the amino acid sequence set forth in SEQ ID NO: 6. Specifically, a useful chimeric polypeptide is the chimeric polypeptide set forth in SEQ ID NO: 1 and the chimeric polypeptide set forth in SEQ ID NO: 3.

The present method additionally provides a method of determining if a subject having a type of diabetes has type I diabetes, comprising (a) contacting a chimeric polypeptide comprising an epitope of GAD65 protein and a structural region comprising a polypeptide of the GAD family, wherein the chimeric polypeptide is a more specific diagnostic for IDDM than intact GAD65 and produces fewer false positives than intact GAD65, with a biological sample from the subject and (b) detecting binding between an antibody in the sample and the chimeric polypeptide, the detection of binding indicating the type of diabetes in the subject is type I diabetes. A subject can be diagnosed as having diabetes by conventional methods, such as by elevated blood sugear levels. The type of diabetes, however, is not necessarily clear from such a test. Therefore, the present inventive assay can be performed to determine if the type of diabetes in the subject is type 1 (IDDM) by detecting the presence in the sample from the subject of GAD autoantibodies. A preferable chimeric polypeptide has a GAD 65 epitope of GAD65 amino acids 270–435 and/or GAD65 amino acids 451–570. The epitope, for example, can have the amino acid sequence set forth in SEQ ID NO: 5 or the amino acid sequence set forth in SEQ ID NO: 6. Specifically, a useful chimeric polypeptide is the chimeric polypeptide set forth in SEQ ID NO: 1 and the chimeric polypeptide set forth in SEQ ID NO: 3. If binding is detected in a subject, indicating the presence oof GAD autoantibodies, therapy/treatment can be prescribed accordingly for type 1 diabetes.

Statement Concerning Utility

GAD autoantibodies are present in the majority of individuals in the prediabetic stage of the disease. Additionally, individuals diagnosed with diabetes who are found to have GAD autoantibodies present can, by the presence of the GAD autoantibodies, be classified as having type 1 diabetes (IDDM). Thus the detection of GAD autoantibodies in an individual can be highly useful, such as to determine if a person is at risk of developing IDDM. Early detection can affect the course of therapy for the individual, and blood levels of insulin can be closely monitored for progression to the disease state. Furthermore, the detection of GAD autoantibodies in an individual can be used to classify the type of diabetes a person has, thereby allowing treatment to be followed according to the specific type of diabetes present. The present chimeric proteins allow for the presentation of the GAD65 epitopes in a manner that allows a high specificity of detection of GAD autoantibodies and can produce fewer false positives than intact GAD65. Such specificity and reduction of false positives therefore provides a much more useful and beneficial reagent for testing for the presence of GAD autoantibodies. Furthermore, the use of such chimeric proteins can allow for the synthesis of chimeric proteins having varied specificities than the native GAD65, which can be useful, for example, to distinguish disease-specific antibodies and disease-specific epitopes, such as for IDDM as distinguished from stiff man syndrome, polyglandular failure type I or a restricted or β-cell-specific islet cell autoantibody (ICA) pattern.

EXAMPLES

The present invention is more particularly described in the following examples which are intended as illustrative only since numerous modifications and variations therein will be apparent to those skilled in the art.

Creation of GAD 65/GAD 67 Chimeric Proteins. To prepare chimeric GAD 65/GAD 67 cDNAs, an unique restriction enzyme site was introduced into the rat GAD 65 cDNA or human GAD 67 cDNA by PCR or site-directed mutagenesis. Introduction of the unique restriction site in the cDNAs did not alter the predicted amino acid sequence and occurred in a stretch of amino acids that were identical in GAD 65 and GAD 67. PCR amplification was performed using either the human GAD 67 or rat GAD 65 plasmid cDNA and primers to incorporate a one-, two-, or three-base pair mutation. Site-directed mutagenesis was performed with the Transformer Mutagenesis system (Clontech, Palo Alto, Calif.). The presence of the mutation introduced by PCR or site-directed mutagenesis was confirmed by dideoxy sequencing. Following introduction of the desired restriction enzyme site into one GAD isoform, a cDNA fragment was exchanged with the corresponding cDNA fragment from the other GAD cDNA to produce a chimeric cDNA by standard subcloning techniques. For the production of GAD RNA, all wild type and chimeric GAD cDNAs were subcloned into the plasmid, pGOV, which contains a T7 RNA polymerase promoter (Ujihara et al. (1994) *Diabetes* 43:968–975).

The following nomenclature for GAD chimera was utilized: GAD 65 or 67 (amino acid number of that GAD species present in the GAD chimera)/GAD 65 or 67 (amino acid number of that GAD species present in the GAD chimera). The GAD 65 protein has 585 amino acids and the GAD 67 protein has 594 amino acids. To create the chimera, GAD 65 (1–195)/GAD 67 (205–594), a Hinc II site was introduced at the appropriate location of the GAD 67 cDNA by PCR and the resulting GAD 67 fragment exchanged with the corresponding fragment of the GAD 65 cDNA (using a native Hinc II site in the GAD 65 cDNA). To create the chimera GAD 67 (1–230)/GAD 65 (221–585), an Afl II was introduced at the appropriate location of the GAD 65 cDNA by PCR and the resulting GAD 65 fragment exchanged with the corresponding fragment of the GAD 67 cDNA (using a native Afl II site in the GAD 67 cDNA). To create the chimera GAD 65 (14–42)/GAD 67 (452–594) and the chimera GAD 67 (1–451)/GAD 65 (443–585), an unique Stu I site was introduced by site-directed mutagenesis in the GAD 67 cDNA. Corresponding cDNA fragments encoding GAD 65 (1–442) and GAD 67 (1–451) were exchanged (using a native Stu I site in the GAD 65 cDNA) to produce the chimera GAD 65 (1–442)/GAD 67 (452–594) and the chimera GAD 67 (1–451)/GAD 65 (443–585). The chimera, GAD 67 (1–230)/GAD 65 (221–442)/GAD 67 (452–594), was created by digesting GAD 67 (1–230)/GAD 65 (221–585) and GAD 65 (1–442)/GAD 67 (452–594) with Stu I and exchanging cDNA fragments. The chimera, GAD 65 (1–195)/GAD 67 (205–441)/GAD 65 (443–585), was created by digesting GAD 65 (1–195)/GAD 67 (205–594) with Afl II and exchanging this fragment with the corresponding fragment in GAD 67 (1–451)/GAD 65 (443–585). Both the Afl II and Stu I sites are unique for GAD 65 and GAD 67, respectively.

The chimeric composition of the GAD cDNAs was confirmed by restriction enzyme digestion and dideoxy DNA sequencing. Following in vitro translation, chimeric proteins were of the expected molecular weight by SDS-PAGE. In addition, chimeric proteins containing the COOH-terminus of GAD 65 reacted with the monoclonal antibody GAD-6 (Chang et al. (1988) *J Neurosci* 8:2123–2130), which is specific for this region of GAD 65 (Ujihara et al. (1994). The GAD-6 monoclonal antibody was obtained from the Developmental Studies Hybridoma Bank at the University of Iowa (NICHD contract # NO 1-HD-2-3144).

Serum Samples. Serum samples were collected from individuals with new-onset diabetes (N=12) and from control, non-diabetic individuals and stored at $-20°$ C. The clinical features of the IDDM sera have been previously described (Ujihara et al. (1994)).

Preparation and Immunoprecipitation of GAD protein. Full-length rat GAD 65, human GAD 67, and the chimeric GAD 65/GAD 67 cDNAs were transcribed into GAD RNA using T7 RNA Polymerase in an in-vitro transcription system (Megascript, Ambion) (Ujihara et al. (1994)). Metabolically-labeled, recombinant GAD protein was prepared by in-vitro translation of GAD RNA with reticulocyte lysate (Promega) using an amino acid mixture containing 35S-Methionine (1200 Ci/mmol) (Ujihara et al. (1994)). For immunoprecipitation, thirty ul of serum (1:1–1:20 dilution) was incubated with 30 ul of metabolically-labeled GAD protein (50,000 cpm) for 12–15 hours at $4°$ C. (Ujihara et al. (1994)). All dilutions of serum and GAD protein were made with Tris-Buffered Saline/0.05% Tween 20 (TBST). Protein A-sepharose (PAS, Sigma) was washed and resuspended in TBST to a 2% solution. Two ul of PAS (final bed volume) was added to the GAD protein/serum reaction and mixed for one hour at $4°$ C. by gentle rotation. The protein A-Sepharose pellets were then washed three times with 500 ul of TBST and resuspended in 100 ul of 1% SDS and counted by beta scintillation counting. All serum samples were assayed in duplicates. The results are presented as the mean+SEM of at least 3 separate experiments. Our laboratory participated in the GAD antibody workshops (Schmidli et al. (1994), *Diabetes* 43:1005–1009) sponsored by the Immunology of Diabetes Workshop (1993, 1994). In the 1994 workshop, our GAD 65 assay was positive in 82% of sera from individuals with new-onset diabetes, 100% of sera from individuals with pre-diabetes, and 3% of normal individuals.

Competitive Inhibition of Antibody Binding to GAD Protein. Unlabeled, full-length GAD 65, GAD 67, and chimeric GAD 65/GAD 67 protein were prepared in the reticulocyte lysate system as detailed above except that the amino acid mixture contained unlabeled methionine rather than 35S-methionine. For the blocking studies, unlabeled GAD protein was incubated with the test serum for 3 hours at room temperature; this mixture was then added to 50,000 cpm of 35S-GAD protein and incubated for 12–15 hours at $4°$ C. (Ujihara et al. (1994)). PAS was added and immuno-precipitation was performed as described above. The immunoprecipitate was analyzed by scintillation counting and expressed as the % GAD protein immunoprecipitated following preincubation with buffer without unlabeled GAD protein. All serum samples were assayed in duplicates. The results are presented as the mean+SEM of at least 3 separate experiments.

IDDM sera bind two regions of GAD 65 protein. Most IDDM sera bind GAD 65, but not GAD 67. Although GAD 65 and GAD 67 difffer substantially in the NH2-terminal third of the protein and the first 8 amino acids of GAD 65 are targeted by antibodies in SMS (Butler et al. (1993) *J. Exp. Med.* 178:2097–2106; Kim et al. (1994) *J. Exp. Med.* 180:595–606), the GAD 65-specific autoantibodies in IDDM sera do not bind a chimeric protein consisting of the NH2-terminal third of GAD 65 and the COOH-terminal two-thirds of GAD 67 [GAD 65 (1–195)/GAD 67 (205–594)]. Conversely, IDDM sera bind the chimera GAD 67 (1–230)/GAD 65 (221–585) in equivalent amounts as full-length GAD 65.

These results indicate that there are two regions of the COOH-terminal two-thirds of GAD 65 that are targeted by IDDM sera. Most IDDM sera bind equal amounts of both GAD 65 (1–442)/GAD 67 (452–594) and GAD 67 (1–451)/GAD 65 (443–585). Some IDDM sera bind more GAD 65 (1–442)/GAD 67 (452–594) than GAD 67 (1–451)/GAD 65 (443–585).

Both regions of GAD protein contribute to total GAD binding in IDDM sera. To further narrow the regions targeted by the autoantibodies and to assess the relative contribution of the two regions to total GAD binding in IDDM sera, two additional GAD chimera, GAD 67 (1–230)/GAD 65 (221–442)/GAD 67 (452–594) and GAD 65 (1–195)/GAD 67 (205–441)/GAD 65 (443–585) were created. Chimera containing only amino acids 221–442 of GAD 65 or a chimera containing amino acids 442–585 of GAD 65 were used to inhibit the binding of IDDM sera to full-length GAD 65. Two patterns of antibody binding in IDDM were observed. In the first pattern, preincubation of IDDM sera with either GAD 67 (1–230)/GAD 65 (221–442)/GAD 67 (452–594) or GAD 65 (1–195)/GAD 67 (205–441)/GAD 65 (443–585) partially inhibited the binding to full-length GAD 65. However, when the sera were preincubated with both chimeric GAD proteins, the binding to full-length GAD 65 was completely inhibited. These results indicate the presence of two distinct antibody specificities which target different regions of GAD 65 and contribute to the total GAD binding in IDDM sera. In the second pattern, only the GAD 67 (1–230)/GAD 65 (221–442)/GAD 67 (452–594) chimera was required to inhibit the binding to full-length GAD 65. This indicates that in this IDDM serum, an antibody specificity for amino acids 221–442 is responsible for total GAD binding. If such sera also contain a second GAD specificity which targets amino acids 443–585, this reactivity is present at a much lower titer. Our findings indicate that at least one antibody targets each region.

Identification of amino acids targeted by IDDM sera. Since GAD 65 and GAD 67 are highly homologous, differences between the two isoforms within the two regions of GAD 65 targeted by IDDM sera may identify amino acids responsible for the binding of IDDM sera to GAD 65, but not GAD 67. After excluding amino acids that are identical in the GAD 65 and GAD 67 isoforms, the two areas of binding can be narrowed to amino acids 240–435, and further to amino acids 270–442, and to amino acids 443–585. The GAD 65 and GAD 67 isoforms are 72% identical and 64% identical in these 2 regions, respectively. Since rat GAD 65 (used for these comparisons) and human GAD 65 are greater than 98% identical in these regions, similar results were found with comparisons of human GAD 65 and human GAD 67. Based on nomenclature suggested by De Camilli and colleagues for GAD epitopes in SMS (Butler et al. (1993) *J. Exp. Med.* 178:2097–2106), the epitope contained in amino acids 240–435 is labeled IDDM-E1, and the epitope contained in amino acids 451–570 are labeled IDDM-E2. Most of the differences in protein sequence in GAD 65 and GAD 67 in the regions of IDDM-E1 and IDDM-E2 are single amino acids. One area of marked difference in the two GAD isoforms is noted in the region of IDDM-E2 (between amino acids 505–517 where 10/13 amino acids are different). Site-directed mutagenesis can provide for precise identification of the amino acids targeted by the GAD antibodies in IDDM sera.

To assess the frequency of GAD antibodies to these two regions, the binding to IDDM-E1 and IDDM-E2 of GAD 65 with sera from individuals with new-onset IDDM (N=12) was measured. Most IDDM sera (N=11/12) bound both IDDM-E1 and IDDM-E2. One IDDM sera bound only IDDM-E1.

The two distinct antibody specificities present in IDDM sera may be identical to the MICA 1 and MICA 3 monoclonal antibodies isolated from a single patient with IDDM by Richter and colleagues (Richter et al. (1993)). Comparative studies with these monoclonal antibodies and IDDM sera can be performed to determine if these monoclonal antibodies derived from a single individual with IDDM are representative of IDDM sera. The contribution of a particular monoclonal antibody species to the total GAD autoantibody pool can then be be estimated. The relative amount of a particular GAD autoantibody species in relation to other autoantibody species must use sera from a number of individuals with IDDM. The newly-created GAD chimera will be useful in such studies.

Implications for IDDM prediction and pathogenesis. GAD antibodies are an important immunologic marker for IDDM, but several groups of GAD antibody-positive individuals with a low risk of developing diabetes have now been recognized (Genovese et al. (1992) *Diabetologia* 35:385–388; Gianani et al. (1992) *Diabetes* 41:347–353; Bjork et al. (1994) *Diabetes* 43:161–165). Differences in the GAD antibody profile can allow one to distinguish between individuals at high and low risk of developing IDDM. With the present identification of regions targeted by IDDM sera, a precise comparison of the GAD antibody profiles can be done and additional chimeric proteins can be generated. As a specific region is found to be targeted by IDDM sera and not by other GAD antibody positive-sera, then a GAD 65/GAD 67 chimera can be used to design additional assays specific for IDDM. In addition, the GAD 65/GAD 67 chimera can be used to determine whether differences in the two distinct GAD antibodies identify subsets of IDDM by correlating the presence or absence of a particular GAD antibody species with other aspects of IDDM such as HLA status, temporal relationship to other markers of autoimmunity, and beta cell function.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A nucleic acid encoding a chimeric polypeptide comprising an epitope or epitores of GAD65 protein, said epitope selected from the group consisting of an epitope present in amino acids 270–435, an epitope present in amino acids 451–570, an epitope present in amino acids 221–585, an epitope present in amino acids 270–442, an epitope present in amino acids 443–513, an epitope present in amino acids 528–585, an epitope present in amino acids 451–585, and an epitope present in amino acids 221–442, and a structural region comprising a polypeptide from a GAD67 protein, wherein the chimeric polypeptide is a more specific diagnostic for insulin dependent diabetes mellitus than intact GAD65 and produces fewer false positives than intact GAD65.

2. The nucleic acid of claim 1, wherein the GAD65 epitope consists of amino acids from amino acid 270 to amino acid 435 of GAD65.

3. The nucleic acid of claim 1, wherein the GAD65 epitope consists of amino acids from amino acid 451 to amino acid 570 of GAD65.

4. The nucleic acid of claim 1, wherein the chimeric polypeptide comprises multiple structural regions of GAD67.

5. The nucleic acid of claim 1, wherein the chimeric polypeptide comprises multiple structural regions of GAD67 and multiple epitopes of GAD65.

6. The nucleic acid of claim 1, wherein the epitope consists of amino acid 270 to amino acid 435 of GAD65 and the GAD67 structural region consists of amino acid 1 to amino acid 230 of GAD 67 and amino acid 452 to amino acid 594 of GAD 67.

7. The nucleic acid of claim 1, wherein the epitope consists of amino acid 270 to amino acid 435 of GAD65 and the GAD67 structural region consists of amino acid 452 to amino acid 594 of GAD 67.

8. The nucleic acid of claim 1, wherein the epitope consists of amino acid 451 to amino acid 570 of GAD65 and the GAD67 structural region consists of amino acid 1 to amino acid 451 of GAD67.

9. A nucleic acid encoding a chimeric polypeptide comprising an epitope of GAD65 inserted into GAD67, said epitope selected from the group consisting of an epitope present in amino acids 270–435, an epitone present in amino acids 451–570, an epitope present in amino acids 221–585, an epitope present in amino acids 270–442, an epitope present in amino acids 443–513, an epitope present in amino acids 528–585, an epitope present in amino acids 451–585, and an epitope present in amino acids 221–442, wherein the GAD65 epitope replaces amino acids of GAD67 corresponding to amino acids of the GAD65 epitope and wherein the chimeric polypeptide is a more specific diagnostic for insulin dependent diabetes mellitus than intact GAD65 and produces fewer false positives than intact GAD65.

10. The nucleic acid of claim 9, wherein the GAD65 epitope comprises GAD65 amino acids 270–435.

11. The nucleic acid of claim 9, wherein the GAD65 epitope comprises GAD65 amino acids 451–570.

* * * * *

UNITED STATES PATENT AND TRADEMARK OFFICE
CERTIFICATE OF CORRECTION

| | |
|---|---|
| PATENT NO. | : 6,060,593 |
| APPLICATION NO. | : 09/028148 |
| DATED | : May 9, 2000 |
| INVENTOR(S) | : Powers |

It is certified that error appears in the above-identified patent and that said Letters Patent is hereby corrected as shown below:

<u>Column 1</u>

Line 11, please delete "an ROI grant" and insert --ROI grant DK043736--

Line 14, please delete "may have" and substitute --has--

Signed and Sealed this

Fifth Day of June, 2007

JON W. DUDAS
*Director of the United States Patent and Trademark Office*